United States Patent [19]

Otto

[11] 4,058,745
[45] Nov. 15, 1977

[54] CONTROLLED GAP SURFACE ACOUSTIC WAVE DEVICE

[75] Inventor: Oberdan W. Otto, Los Angeles, Calif.

[73] Assignee: Hughes Aircraft Company, Culver City, Calif.

[21] Appl. No.: 702,570

[22] Filed: July 6, 1976

[51] Int. Cl.$^2$ .............................................. H01L 41/04
[52] U.S. Cl. ................................. 310/366; 364/821
[58] Field of Search ............... 310/8.1, 9.8; 333/30 R, 333/72; 330/5.5; 235/181

[56] References Cited

U.S. PATENT DOCUMENTS

| 3,906,409 | 9/1975 | Whitehouse | 310/9.8 X |
| 3,917,401 | 11/1975 | Stolwyk | 310/9.8 X |
| 3,944,732 | 3/1976 | Kino | 310/9.8 X |

OTHER PUBLICATIONS

Acoustic Surface Waves, by Kino & Shaw, *Scientific American*, vol. 227, No. 4, Oct. 1972, pp. 51-68.

Primary Examiner—Mark O. Budd
Attorney, Agent, or Firm—John Holtrichter, Jr.; W. H. MacAllister

[57] ABSTRACT

A surface acoustic wave device for use as an amplifier or convolver, or the like, and incorporating a plurality of parallel, spaced rails disposed between and separating a semiconductor slab and a surface acoustic wave propagating planar surface of a piezoelectric substrate a relatively small but finite distance apart, the rails having longitudinal axes aligned with the propagation beam path by and between a pair of spaced electro-acoustic transducers disposed on the substrate.

9 Claims, 3 Drawing Figures

CONTROLLED GAP SURFACE ACOUSTIC WAVE DEVICE

BACKGROUND OF THE INVENTION

The background of the invention will be set forth in two parts.

Field of the Invention

This invention relates to surface acoustic wave devices and more particularly to surface acoustic wave amplifiers and convolvers.

Description of the Prior Art

An important type of surface acoustic wave amplifier and convolver involves the coupling of surface acoustic wave energy propagating on a polished surface of a piezoelectric substrate to a semiconductor slab spaced a short distance away. Specifically there has long been a need for supporting a semiconductor slab less than about 1000 A from a polished piezoelectric crystal surface over dimensions of about 1 mm wide by 2 to 3 cm long.

The basic problem is to maintain a close and uniform spacing between the substrate surface and the lower surface of the semiconductor slab without introducing separating structure which will overly attenuate the propagating energy or cause coherent scattering. In the past, various schemes have been proposed to accomplish this configuration, but most have been found to have serious disadvantages.

One solution is to avoid locating anything in the beam path which could cause attenuation, distortion or beam scattering by supporting the slab on two rails, one on each side of the surface acoustic wave beam path. Here, the rails may be 0.1 μm high and were separated by the width of a 1 mm beam path. This gives a 10,000:1 aspect ratio of rail separation to height. Uniform gap dimensions have proved to be very difficult to maintain, and there is a tendency for the slab to bow inwardly and contact the piezoelectric surface which is undesirable because it severely attenuates and distorts the acoustic beam.

Another proposed solution to this problem is to have a large number of pseudo-randomly positioned "posts" to hold these two media apart. The pseudo-random positioning avoids coherent scattering and wavefront distortion of the propagating wave energy from the posts; however, the generation of such a pattern to be sure there is a uniform average density is in itself a difficult problem to solve. Furthermore, fabrication of a mask without repeating sections (hence introducing a periodicity) is very costly. Additional information on the subject of pseudo-randomly positioned "posts" may be obtained by making reference to an article in the 1975 Ultrasonics Symposium Proceedings, IEEE Cat. #75 CHO 994-4SU, entitled "Techniques for Making Gap-Coupled Acoustoelectric Devices," by Henry I. Smith.

From the foregoing it should be evident that a technique which provides for uniform close spacing of a semiconductor slab over a polished surface of a piezoelectric substrate without introducing coherent scattering, wavefront distortion or severe attenuation, would constitute a significant advancement in the art.

SUMMARY OF THE INVENTION

In view of the foregoing factors and conditions characteristic of the prior art, it is a primary object of the present invention to provide a new and improved controlled gap surface acoustic wave device.

Another object of the present invention is to provide an easily-produced, simple yet effective controlled gap surface acoustic wave device which may be easily configured to operate either as an acousto-electric surface acoustic wave amplifier or a convolver.

Still another object of the present invention is to provide an efficient controlled gap surface acoustic wave device having a uniform gap between a semiconductor slab and a surface acoustic wave propagating surface of a piezoelectric substrate and which utilizes support means for the slab that is very easy to design and the mask for which is easy to generate because it uses repeating sections.

In accordance with one embodiment of the present invention, a surface acoustic wave device incorporating a controlled gap and adaptable for use as a convolver, or amplifier, or the like, is provided. Disposed on a substrate of piezoelectric material having a polished upper surface capable of propagating surface acoustic wave energy are a pair of spaced electro-acoustic transducers for defining a propagation beam path between the transducers. Also included is a semiconductor slab having a lower polished planar surface and an upper planar surface at least partially in contact with a conductive electrode. Disposed between the transducers are a plurality of parallel spaced elongated rails having longitudinal axes aligned with the propagation beam path for separating the upper planar surface of the substrate and the lower planar surfce of the slab a predetermined distance to couple surface acoustic wave energy propagating in the beam path to the slab. Pressure means for exerting a uniform compressional force is coupled to the slap and to the substrate forcing these two elements together, while contact therebetween is prevented by the rails.

The rails may be provided by ion beam etching or by plasma etching and the like into the substrate or by a thin-film deposition technique, for example. Generally, the height of the rails is less than or approximately equal to the wavelength of the propagating surface acoustic wave energy divided by $2\pi$ times the effective relative dielectric coefficient of the substrate material for a given crystal cut and propagation direction. Also, the aspect ratio of periodicity to height of the rails is preferably less than about 1,000:1, and the ratio of rail width to periodicity is less than or equal to about 0.2.

The features of the present invention which are believed to be novel are set forth with particularity in the appended claims. The present invention, both as to its organization and manner of operation, together with further objects and advantages thereof, may best be understood by making reference to the following description taken in conjunction with the accompanying drawings, in which like reference characters refer to like elements in the several views.

DESCRIPTION OF THE PREFERRED EMBODIMENTS

Figure 1:
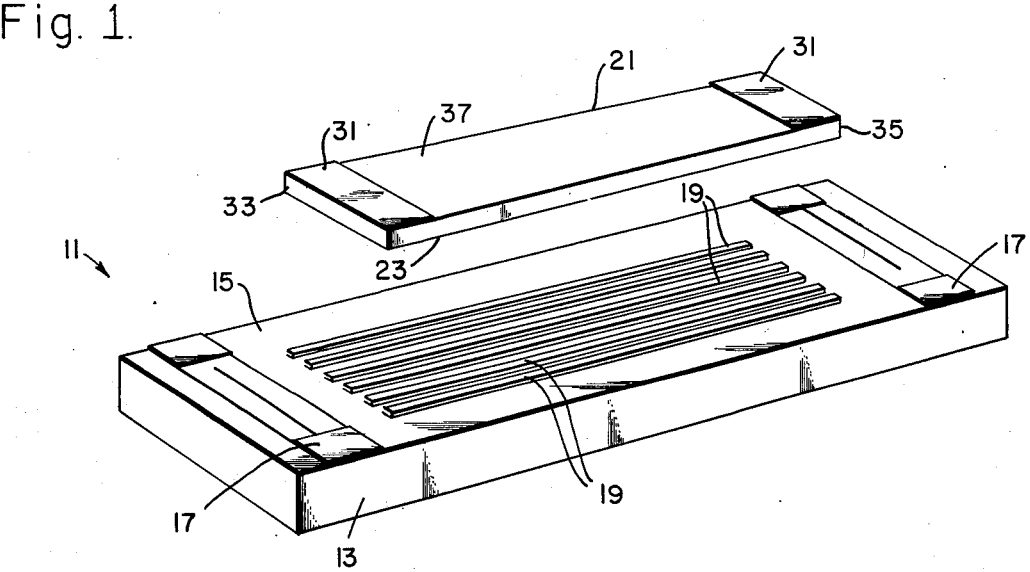
FIG. 1 is a perspective view of a controlled gap surface acoustic wave device configured as an electroacoustic amplifier and showing the semiconductor slab raised above the substrate to better illustrate the supporting rail configuration.
Figure 2:
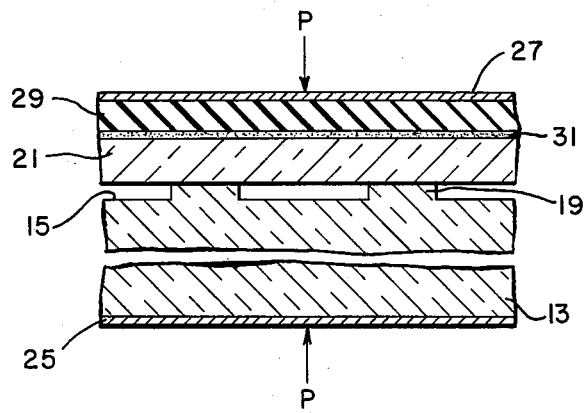
FIG. 2 is a sectional view of a controlled gap surface acoustic wave device taken transversely to the propagation beam path along line 2—2 of FIG. 1.

Referring now to the drawing and more particularly to FIGS. 1 and 2, there is shown a controlled gap surface acoustic wave device 11 for use as an amplifier. The device 11 includes a piezoelectric substrate 13 having an upper polished planar surface 15 capable of supporting propagating surface wave energy generated by either or both of the conventional interdigitated electroacoustic transducers 17 which generally define a surface acoustic wave beam path between them. In this embodiment either one of the transducers 17 may be an input transducer for converting an electromagnetic signal to surface acoustic wave energy, while the other functions as an output transducer which converts surface acoustic wave energy incident thereon into an electromagnetic signal.

The substrate may be fabricated from a material such as Y-cut Z-propagating lithium niobate (LiNbO$_3$) and the transducers 17 may be any conductive material such as aluminum, gold, silver, and the like, disposed in spaced relationship on the surface 15 by any conventional process, such as vacuum deposition, for example.

Located on the substrate surface 15 between the transducers 17 are a plurality of spaced parallel elongated supporting elements or rails 19. The rails are colinear with the aforementioned propagation path and are adapted to support a slab 21 of semiconductor material, such as, for example, epitaxial $n$ on $n^+$ Si. In the embodiment shown in FIGS. 1 and 2, the rails are 6 $\mu$m wide on 25 $\mu$m centers with the surface of the LiNbO$_3$ ion-beam etched down 0.06 $\mu$m. Alternately, the rails 19 may be thin-film deposited, and may be of a semiconductive, conductive or insulative material. Thus, it can be seen that as far as the propagating surface acoustic wave energy is concerned, essentially the main dielectric separating the lower planar surface 23 of the semiconductor slab 21 and the upper planar surface 15 of the piezoelectric substrate 13 is air. Preferably, the rails 19 are equally spaced, which periodicity facilitates the design, masking and generation of the rails.

FIG. 2 further illustrates that a pressure P is provided to the slab and substrate combination forcing these two elements toward each other. In this embodiment, the pressure is evenly distributed to these elements through a bottom plate 25 and a top plate 27 acting through a pad 29 of a resilient material such as rubber, for example. The force need not exceed a few pounds per square inch and may be provided by means of weights, or a clamp, or any other conventional manner. Thus, the two media are squeezed together and the two adjacent planar surfaces 15 and 23 will conform to one another while the rails 19 prevent them from touching.

This inventive technique allows the maintaining of the two media a small but finite distance from each other in a controlled manner over a relatively large area. Specifically, this technique has provided, for example, the supporting of a semiconductor less than 1000 A (and as little as 500 A) from a polished piezoelectric crystal surface over an area of about 1 mm wide by 3 cm long.

The difficulties of the prior art relating to bowing has been overcome in the present invention by utilizing in aspect ratio of rail spacing-to-rail height of the order of 1,000 or 2,000 to 1 or less. Like the prior art pseudorandom positioning of "posts," the parallel rails of the invention avoid coherent scattering of the propagating wave energy but are much simpler to implement.

In accordance with the preferred embodiments of the invention, the height of the rails h may be expressed as $$h \leq \lambda/2\pi e_p \qquad (1)$$

where $\lambda$ is the wavelength of the operating frequency of the surface acoustic wave energy, and $e_p$ is the effective relative dielectric coefficient for a given piezoelectric crystal cut and propagation direction. For Y-cut, Z-propagating LiNbO$_3$, $e_p$ is approximately equal to 50. Additional information relating to separation distance between the piezoelectric substrate and the semiconductor slab may be obtained from an article entitled "A Normal Mode Theory for the Rayleigh Wave Amplifier" by Gordon S. Kino and Thomas M. Reeder in IEEE Transactions on Electron Devices, October 1971.

The preferred aspect ratio a for the rails is given by $$a = p/h, \qquad (2)$$

where $p$ is the period of the rails. In order not to overly attenuate propagating beam energy, the rail width-to-period ratio is preferably, but not limited to 20% or less. That is $$w/p \leq 0.2. \qquad (3)$$

Figure 3:
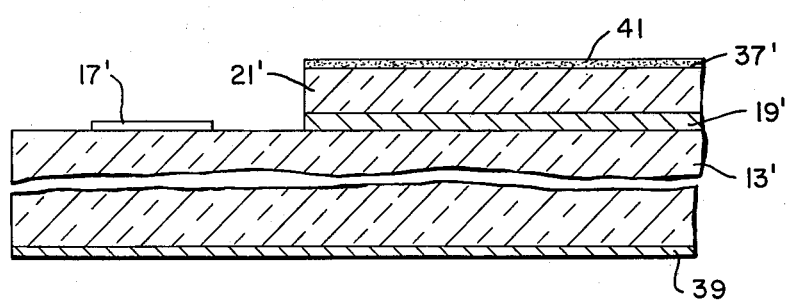
FIG. 3 is a longitudinal sectional view of a controlled gap surface acoustic wave device illustrating a convolver configuration in accordance with another embodiment of the present invention.

The thickness of the semiconductor slab 21 is not critical, but should be thin enough so that with the moderate compressive force mentioned previously, the slab will conform to slow topographical variations in the upper planar surface 15 of the piezoelectric substrate. Typically, the thickness of the semiconductor slab 21 is in the range of from 5 to 10 mils, and has a surface area of 1 cm$^2$ or more.

Where the invention is to be operated as an acoustoelectric surface acoustic wave amplifier, as illustrated in FIGS. 1 and 2, ohmic contact areas 31 are disposed by any conventional process on opposite ends 33, 35 of the upper surface 37 of the slab 21. However, the invention may also be configured as a surface acoustic wave convolver (nonlinear surface acoustic wave convolution filter) as shown in FIG. 3. Here, a conductive plate or ground plane is disposed at the lower planar surface 39 of the piezoelectric substrate 13', and a conductive upper plate 41 is disposed covering essentially all the upper surface 37' of the semiconductor slab 21'. For the sake of clarity, leads are not shown connected to the transducers, and other electrodes. Although not illustrated in FIG. 3, this embodiment also is provided with a means for compressing together the slab and substrate elements, and parallel rails 19' maintain the small separation required between these media. Of course, in a convolver configuration, both transducers 17' are input transducers which convert electromagnetic energy to surface acoustic wave energy along a colinear path into the interaction region between the semiconductor slab 21 and the piezoelectric substrate 13. In an actual reduction to practice of a convolver constructed in accordance with the present invention, the rails produced no observable distortion of the surface acoustic wave wavefront (beam profile probed), and the enhancement of the convolution interaction agreed with the theoretical prediction for a uniform 0.06 μm gap. The interaction region was found to be very uniform for a 2 cm length and excellent quality correlations were obtained.

From the foregoing it should be evident that there have been described novel and extremely useful surface acoustic wave devices which significantly advance the state of the art.

Although specific materials and processes have been herein described, it should be understood that other materials and processes providing similar desired characteristics and configurations may be substituted for those specified.

What is claimed is:

1. A surface acoustic wave device incorporating a controlled gap and adaptable for use as a convolver, amplifier, and the like, comprising:
   a substrate of piezoelectric material having a polished upper surface capable of propagating surface acoustic wave energy;
   transducer means including a pair of spaced electroacoustic transducers disposed on said substrate for defining a propagation beam path between said transducers;
   a semiconductor slab having a lower polished planar surface and an upper planar surface at least partially in contact with a conductive electrode;
   support means including a plurality of parallel, spaced elongated rails disposed on said propagation beam path between said transducers and having longitudinal axes aligned with said propagation beam path for separating said upper and lower planar surfaces a predetermined distance to couple surface acoustic wave energy propagating in said beam path to said slab; and
   pressure means coupled to said slab and to said substrate for exerting a uniform compressional force thereto forcing said planar surfaces toward each other while contact therebetween being prevented by said rails.

2. The device according to claim 1, wherein said rails are ion etched into said substrate.

3. The device according to claim 1, wherein said rails are thin-film deposits on said substrate.

4. The device according to claim 1, wherein the height $h$ of said rails is less than or approximately equal to the wavelength of said propagating surface acoustic wave energy divided by $2\pi$ times the effective relative dielectric coefficient $e_p$ of the substrate material for a given crystal cut and propagation direction.

5. The device according to claim 4, wherein the aspect ratio a comparing the periodicity p of said rails and the rail height $h$ is less than about 1,000 to 1.

6. The device according to claim 5, wherein the ratio of width w to periodicity $p$ is less than or equal to about 0.2.

7. The device according to claim 1, wherein the thickness of said slab allows conformation thereof to slow topographical variations in said upper planar surface of said substrate.

8. The device according to claim 1, wherein the opposite end regions of said upper planar surface are in ohmic contact with separate conductive electrodes, said device being operated as an amplifier.

9. The device according to claim 1, wherein said substrate includes a lower planar surface, wherein approximately the entire area of said upper planar surface is in ohmic contact with a first electrode, and wherein approximately the entire area of said lower planar surface of said substrate is in ohmic contact with a second electrode, said device being operated as a convolver.

* * * * *